United States Patent [19]

Ilgner et al.

[11] Patent Number: 4,592,806

[45] Date of Patent: Jun. 3, 1986

[54] PROCESS FOR THE PRODUCTION OF GRADE AA METHANOL

[75] Inventors: Hartmut Ilgner; Natarajan Thiagarajan, both of Dortmund; Günter Heck, Wiesbaden; Aladar Lienerth, Kelkheim, all of Fed. Rep. of Germany

[73] Assignee: Uhde GmbH, Fed. Rep. of Germany

[21] Appl. No.: 594,287

[22] Filed: Mar. 28, 1984

[30] Foreign Application Priority Data

Mar. 29, 1983 [DE] Fed. Rep. of Germany ....... 3311316

[51] Int. Cl.$^4$ ............................................. B01D 3/14
[52] U.S. Cl. ...................................... 203/71; 203/18; 203/99; 203/DIG. 19; 203/DIG. 23; 568/913
[58] Field of Search ................... 203/DIG. 23, 14, 18, 203/19, DIG. 13, 71, 75, 78, 80, 99, 27, 25, DIG. 19, 77; 568/913, 918, 916

[56] References Cited

U.S. PATENT DOCUMENTS

| | | | |
|---|---|---|---|
| 3,230,156 | 1/1966 | Katzen | 203/93 |
| 3,391,064 | 7/1968 | Akell | 203/83 |
| 3,406,100 | 10/1968 | Karafian | 203/79 |
| 3,434,937 | 3/1969 | Elliot et al. | 203/83 |
| 3,442,770 | 5/1969 | Wentworth et al. | 203/79 |
| 3,884,770 | 5/1975 | Misselhorn | 203/96 |
| 4,013,521 | 3/1977 | Scott | 203/18 |
| 4,210,495 | 7/1980 | Pinto | 203/DIG. 23 |

FOREIGN PATENT DOCUMENTS

| | | | |
|---|---|---|---|
| 0123926 | 9/1981 | Japan | 568/913 |
| 1280438 | 7/1972 | United Kingdom | 203/79 |

Primary Examiner—S. Leon Bashore
Assistant Examiner—V. Manoharan
Attorney, Agent, or Firm—Marshall & Melhorn

[57] ABSTRACT

The invention relates to a process for the production of grade AA methanol by distilling raw methanol in several distillation stages, for separating grade AA methanol, tail gas, and fusel oil from the raw methanol and further processing the fusel oil to produce additional methanol of grade AA quality at a return ratio of 5:1 or higher.

5 Claims, 3 Drawing Figures

PROCESS FOR THE PRODUCTION OF GRADE AA METHANOL

BACKGROUND OF THE INVENTION

The invention relates to a process for refining raw methanol and more particularly to a process for producing grade AA methanol by distilling raw methanol in several distillation stages for separating the raw methanol into grade AA methanol; tail gas and fusel oil.

Processes are known in which raw or crude methanol comprised of methanol and other components is distilled in two stages. In the first staged called a "topping stage", the components having boiling points lower than the boiling point of methanol, such as water, are separated in the second stage called a "refining stage" which consists of one or more distillation columns. However, this separation method causes a change of the concentration profile methanol/ethanol/water/pressure. In order to ensure the specified methanol quality which requires, for instance, a maximum ethanol content of 10 ppm by weight, it is necessary to provide a draw-off nozzle in the intermediate stripping section of each distillation column. The product drawn off, called "fusel oil", is a mixture of methanol, water and higher alcohols such as ethanol, propanol, etc. The fusel oil has such a high methanol content that the methanol losses, referred to the methanol content of the raw methanol produced in synthesis plants, amount to approximately 1.5% of the methanol production.

SUMMARY OF THE INVENTION

The object of the invention is to reduce the methanol losses due to the amount of methanol contained in the fusel oil.

The object of the invention is achieved by distilling the fusel oil produced in the refinishing stages at a return or reflux ratio of at least 5:1 or higher.

The process according to the invention reduces the methanol losses from 1.5% to 0.2% referred to the methanol content of the raw methanol from synthesis plants. The energy required for this process is much cheaper than the value of the methanol recovered. By the above method, it is possible to recover as much as approximately 30 tpd in a methanol synthesis plant with a capacity of 2000 tpd.

According to the invention, the return product required for the fusel oil distillation stage is withdrawn from the last methanol distillation stage in contrast to the first topping stage in order to ensure low energy consumption.

BRIEF DESCRIPTION OF THE DRAWINGS

An embodiment of the invention is illustrated in the accompanying drawings and described in more detail below when considered in light of the drawings, in which.

DETAILED DESCRIPTION OF THE PREFERRED EMBODIMENT

Figure 1:
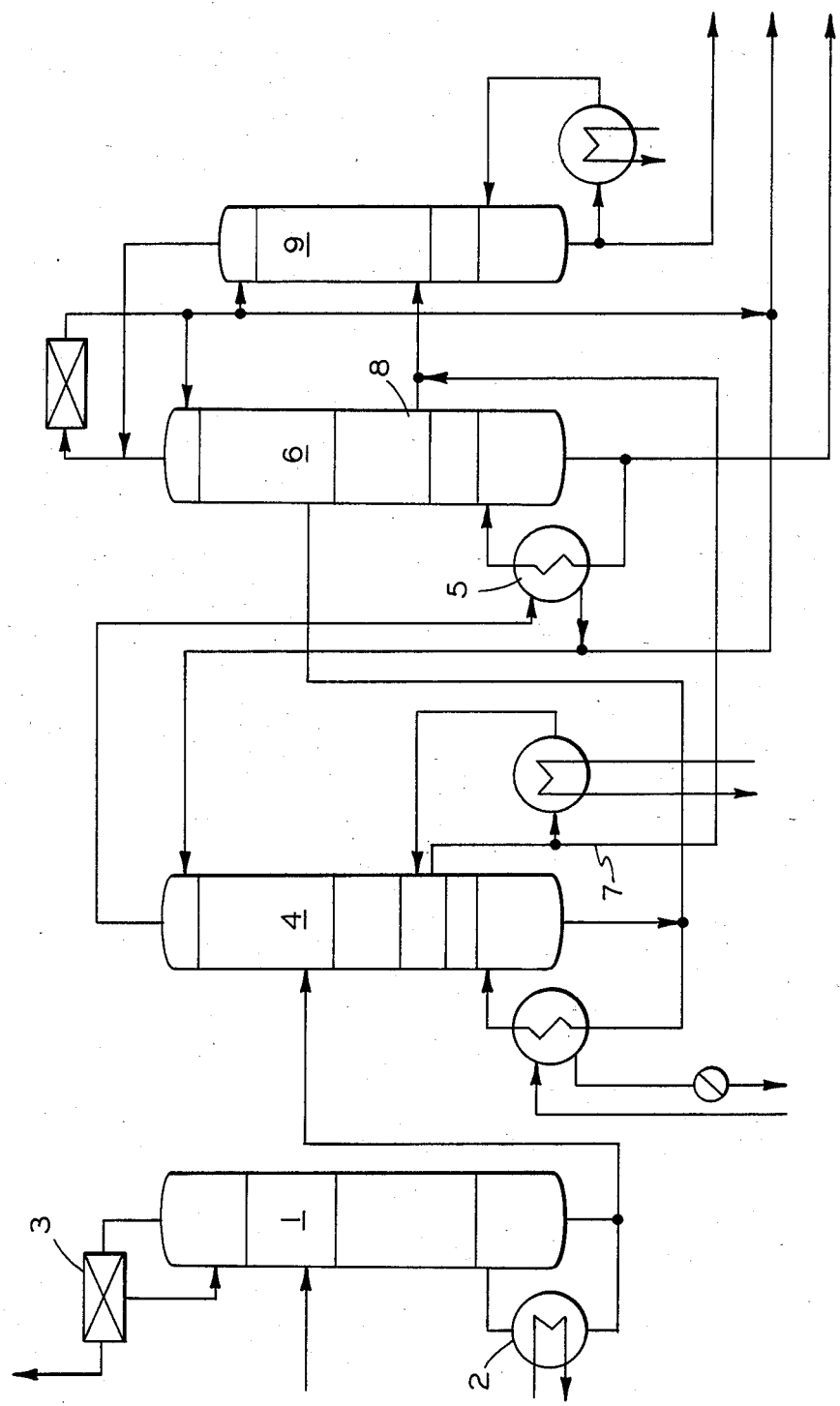
FIG. 1 is a flow chart of a raw methanol distillation plant.

Referring now to FIG. 1, raw methanol is fed to a "topping column" 1 and heated in a downstream heat exchanger 2. The low-boiling components of the raw methanol are withdrawn from the column head and separated from the entrained methanol in a condenser 3 as tail gas. This pre-purified raw methanol is withdrawn from the bottom of the topping column 1 and fed to a refining stage I defined by column 4. The product leaving the top of the column 4 is used for a heating reboiler 5 disposed upstream of a column 6 defining a refining stage II where the product leaving from the bottom of column 4 is distilled.

A certain part of the condensate which is formed from the heat exchange medium used at reboiler 5 is recycled and the remaining part is pure methanol of grade AA. The fusel oil which is produced in refining stage I is withdrawn from column 4 via a pipeline 7.

The product leaving from the top of column 6 condenses in an air-cooled condenser and is partly recycled partly recovered as pure methanol. The product leaving from the bottom of column 6 mainly consists of water which can be used further. The fusel oil withdrawn from the stripping section of column 6 via a pipeline 8 and the fusel oil piped via line 7 are jointly fed to a methanol recovery unit 9. Since this plant has a high recycle rate, the residual MEOH can be well separated. The methanol product corresponds to grade AA and the bottom product in the form of fusel oil is processed further.

Figure 2A:
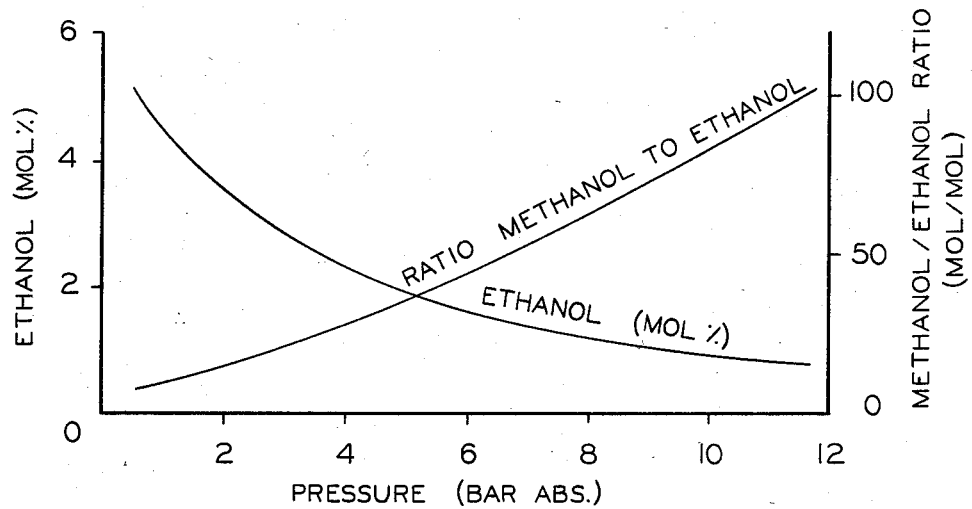
FIG. 2a is a diagram of the methanol losses as a function of the system pressure.
Figure 2B:
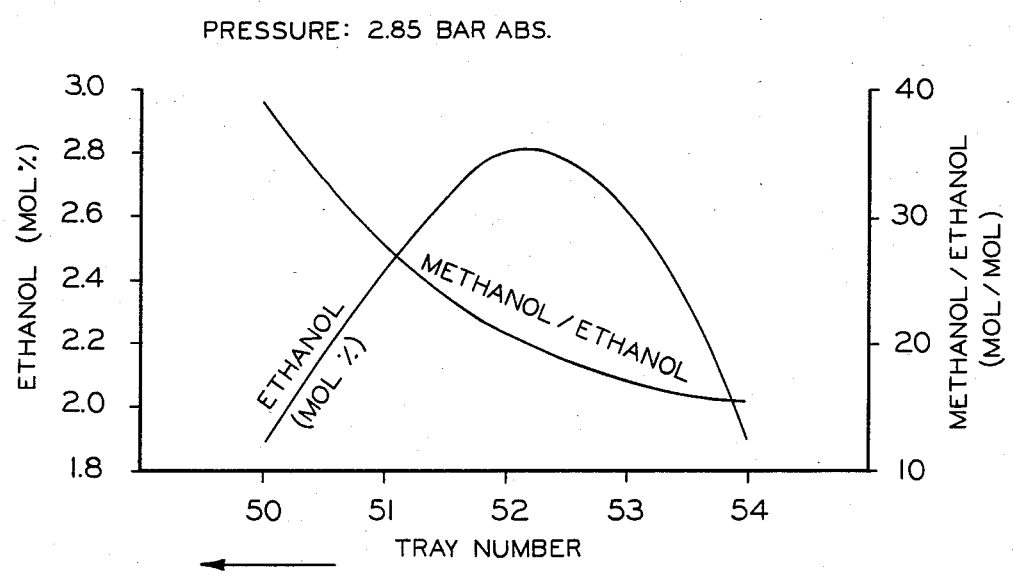
FIG. 2b is a diagram of the concentration profile in the stripping column of the refining stage.

FIGS. 2a and 2b show the characteristic curves of the mixtures concerned. In FIG. 2a, for example, the methanol content is 2.8 mol % and the methanol/ethanol ratio is 22.1 at a system pressure of 2.85 bar abs. The diagram in FIG. 2b indicates that the maximum ethanol content is found in the 52nd tray of the stripping column. In this case, the methanol/ethanol ratio is very low.

What is claimed is:

1. In a method of making Grade AA methanol having a maximum ethanol content of 10 ppm, the method including feeding crude methanol to a first topping distillation column, and using a second distillation column and a third distillation column, in which each of the columns has an intermediate stripping section and the Grade AA methanol being withdrawn from the top level of each of the second and third distillation columns, the improvement comprising removing fusel oil containing methanol from the stripping section of the second column and the stripping section of the third column, and feeding the fusel oil from the second and third columns to a fourth distillation column to recover additional Grade AA methanol from the fusel oil to thereby increase the overall yield Grade AA methanol and distilling the fusel oil at a reflux ratio of at least 5:1 to provide additional methanol product to reduce the methanol loses from about 1.5% to as low as 0.2%.

2. A method as defined in claim 1 in which additional amount of Grade AA methanol recovered in the fourth column is as much as about 30 tons per day in a process making 2,000 tons per day.

3. A process for the production of Grade AA methanol having a maximum ethanol content of 10 ppm, the process comprising the steps of:

(a) distilling crude methanol in several stages including a first topping distillation column, a second distillation column and a third distillation column, in which each of the column has an intermediate stripping section, to provide Grade AA methanol;

(b) removing fusel oil from the stripping section of each of the second and third distillation columns; and (c) distilling the fusel oil removed in step (b) in a fourth distillation column to provide additional Grade AA methanol to thereby reduce the amount of methanol loses encountered in step (a).

4. A process as defined in claim 3 in which the reflux ratio in step (c) is at least about 5:1.

5. In a process for distilling crude methanol to provide Grade AA methanol having a maximum ethanol content of 10 ppm, the method including distilling the crude methanol in a first topping distillation column and withdrawing methanol from the column bottom, the low-boiling components being withdrawn as tail gas, the method further including distilling the methanol from the topping column in a second distillation column and a third distillation column, wherein each of the column has an intermediate stripping section, the Grade AA methanol being removed from the second and third columns as an overhead product, there being water removed from the bottom of each of the second and third columns, the improvement comprising the steps of:

(a) removing from the stripping sections of the second and third columns fusel oil containing methanol, water, ethanol and propanol; and (b) distilling the fusel oil of step (a) in a fourth distillation column to provide an overhead product that is Grade AA methanol that increases the yield of Grade AA methanol in the overall method.

* * * * *